(12) United States Patent
Tang et al.

(10) Patent No.: US 11,878,231 B2
(45) Date of Patent: Jan. 23, 2024

(54) WEARABLE DEVICE AND METHOD FOR CONTROLLING WEARABLE DEVICE

(71) Applicant: Guangdong COROS Sports Technology Joint Stock Company, Guangdong (CN)

(72) Inventors: Yu Tang, Guangdong (CN); Xuan Rao, Guangdong (CN); Cheng Long, Guangdong (CN); Zheng Wu, Guangdong (CN); Tianming Song, Guangdong (CN)

(73) Assignee: GUANGDONG COROS SPORTS TECHNOLOGY JOINT STOCK COMPANY, Guangdong (CN)

( * ) Notice: Subject to any disclaimer, the term of this patent is extended or adjusted under 35 U.S.C. 154(b) by 90 days.

(21) Appl. No.: 17/576,175

(22) Filed: Jan. 14, 2022

(65) Prior Publication Data

US 2022/0241670 A1 Aug. 4, 2022

(30) Foreign Application Priority Data

Feb. 2, 2021 (CN) .......................... 202110143839.0

(51) Int. Cl.
*A63B 71/06* (2006.01)
*G16H 40/67* (2018.01)
*A63B 24/00* (2006.01)
*G06F 1/16* (2006.01)
*G07C 1/22* (2006.01)

(52) U.S. Cl.
CPC ...... *A63B 71/0622* (2013.01); *A63B 24/0062* (2013.01); *G06F 1/163* (2013.01); *G07C 1/22* (2013.01); *G16H 40/67* (2018.01); *A63B 2071/0661* (2013.01); *A63B 2220/12* (2013.01); *A63B 2220/30* (2013.01); *A63B 2220/62* (2013.01); *A63B 2220/73* (2013.01); *A63B 2220/74* (2013.01); *A63B 2225/50* (2013.01)

(58) Field of Classification Search
None
See application file for complete search history.

(56) References Cited

U.S. PATENT DOCUMENTS

2017/0056724 A1* 3/2017 Baker .................... G01S 19/19
2018/0321640 A1* 11/2018 Miyoshi ............... G06F 3/0362

FOREIGN PATENT DOCUMENTS

| CN | 105311815 A | 2/2016 |
| CN | 105380604 A | 3/2016 |
| CN | 108803780 A | 11/2018 |
| CN | 111450504 A | 7/2020 |

* cited by examiner

*Primary Examiner* — Kristy A Haupt
(74) *Attorney, Agent, or Firm* — Michael Best & Friedrich LLP

(57) ABSTRACT

Provided is a method for controlling a wearable device. The method includes acquiring a first time stamp, where the first time stamp is a time at which a user starts climbing; calculating a single-lap climbing altitude of the user according to data of a barometer; acquiring a second time stamp according to a preset single-lap altitude and the single-lap climbing altitude; calculating a climbing time according to the first time stamp and the second time stamp; and calculating a single-lap vertical velocity according to the climbing time and the single-lap altitude.

12 Claims, 5 Drawing Sheets

WEARABLE DEVICE AND METHOD FOR CONTROLLING WEARABLE DEVICE

CROSS-REFERENCE TO RELATED APPLICATION(S)

This application claims priority to Chinese Patent Application No. 202110143839.0 filed Feb. 2, 2021, the disclosure of which is incorporated herein by reference in its entirety.

TECHNICAL FIELD

The present application relates to the field of wearable devices and, in particular, to a wearable device and a method for controlling the wearable device.

BACKGROUND

In mountaineering, skiing, parachuting, diving and other sports based on vertical displacement, the exercise amount for the activity is usually measured by the total amount of change in altitude. For example, as climbing an alpine with an altitude of 4,000 meters and starting from a platform with an altitude of 2,000 meters, a total climbing amount is 2,000 meters. Existing sports data recording devices, including a mobile phone, an outdoor global positioning system (GPS) handset, a sports watch and the like, use the GPS positioning technology to calculate a horizontal displacement distance between two points of the athlete in a period of time. However, the current movement process is measured by the distance, which cannot reflect the actual exercise situation of the athlete.

SUMMARY

In one aspect, the present application provides a method for controlling a wearable device. The method includes the following steps: a first time stamp is acquired, where the first time stamp is a time at which a user starts climbing; a single-lap climbing altitude of the user is calculated according to data of a barometer; a second time stamp is acquired according to a preset single-lap altitude and the single-lap climbing altitude; a climbing time is calculated according to the first time stamp and the second time stamp; and a single-lap vertical velocity is calculated according to the climbing time and the single-lap altitude.

In some embodiments, the single-lap climbing altitude is a climbing altitude of the user within a single lap.

In some embodiments, the step in which the first time stamp is acquired includes the following steps: multiple sampling points are acquired from the barometer; an accumulated altitude change of the multiple sampling points is calculated; and the first time stamp is determined according to the accumulated altitude change and a first threshold.

In some embodiments, the step in which the second time stamp is acquired includes the following step: the second time stamp is determined in response to determining that a difference between the single-lap altitude and the single-lap climbing altitude is less than or equal to a second threshold.

In some embodiments, the method further includes the following step: a real-time vertical velocity of the user is calculated according to a preset time window.

In some embodiments, the method further includes the following step: the data of the barometer is filtered according to the real-time vertical velocity.

In another aspect, the present application provides a wearable device. The wearable device includes a barometer and a processor. The processor is configured to acquire a first time stamp, where the first time stamp is a time at which a user starts climbing; calculate a single-lap climbing altitude of the user according to data of a barometer; acquire a second time stamp according to a preset single-lap altitude and the single-lap climbing altitude; calculate a climbing time according to the first time stamp and the second time stamp; and calculate a single-lap vertical velocity according to the climbing time and the single-lap altitude.

In some embodiments, the single-lap climbing altitude is a climbing altitude of the user within a single lap.

In some embodiments, the processor is further configured to acquire multiple sampling points from the barometer; calculate an accumulated altitude change of the multiple sampling points; and determine the first time stamp according to the accumulated altitude change and a first threshold.

In some embodiments, the processor is further configured to determine the second time stamp in response to determining that a difference between the single-lap altitude and the single-lap climbing altitude is less than or equal to a second threshold.

In some embodiments, the processor is further configured to calculate a real-time vertical velocity of the user according to a preset time window.

In some embodiments, the processor is further configured to filter the data of the barometer according to the real-time vertical velocity.

In another aspect, the present application provides a non-transitory computer-readable storage medium. The non-transitory computer-readable storage medium stores a computer instruction, wherein the computer instruction, when executed by a processor, enable the processor to execute a method for controlling a wearable device, and the method includes the following steps: a first time stamp is acquired, where the first time stamp is a time at which a user starts climbing; a single-lap climbing altitude of the user is calculated according to data of a barometer; a second time stamp is acquired according to a preset single-lap altitude and the single-lap climbing altitude; a climbing time is calculated according to the first time stamp and the second time stamp; and a single-lap vertical velocity is calculated according to the climbing time and the single-lap altitude.

BRIEF DESCRIPTION OF DRAWINGS

To illustrate the technical schemes in the embodiments of the present application more clearly, the accompanying drawings used in the embodiments of the present application will be described below.

DETAILED DESCRIPTION

Figure 1:
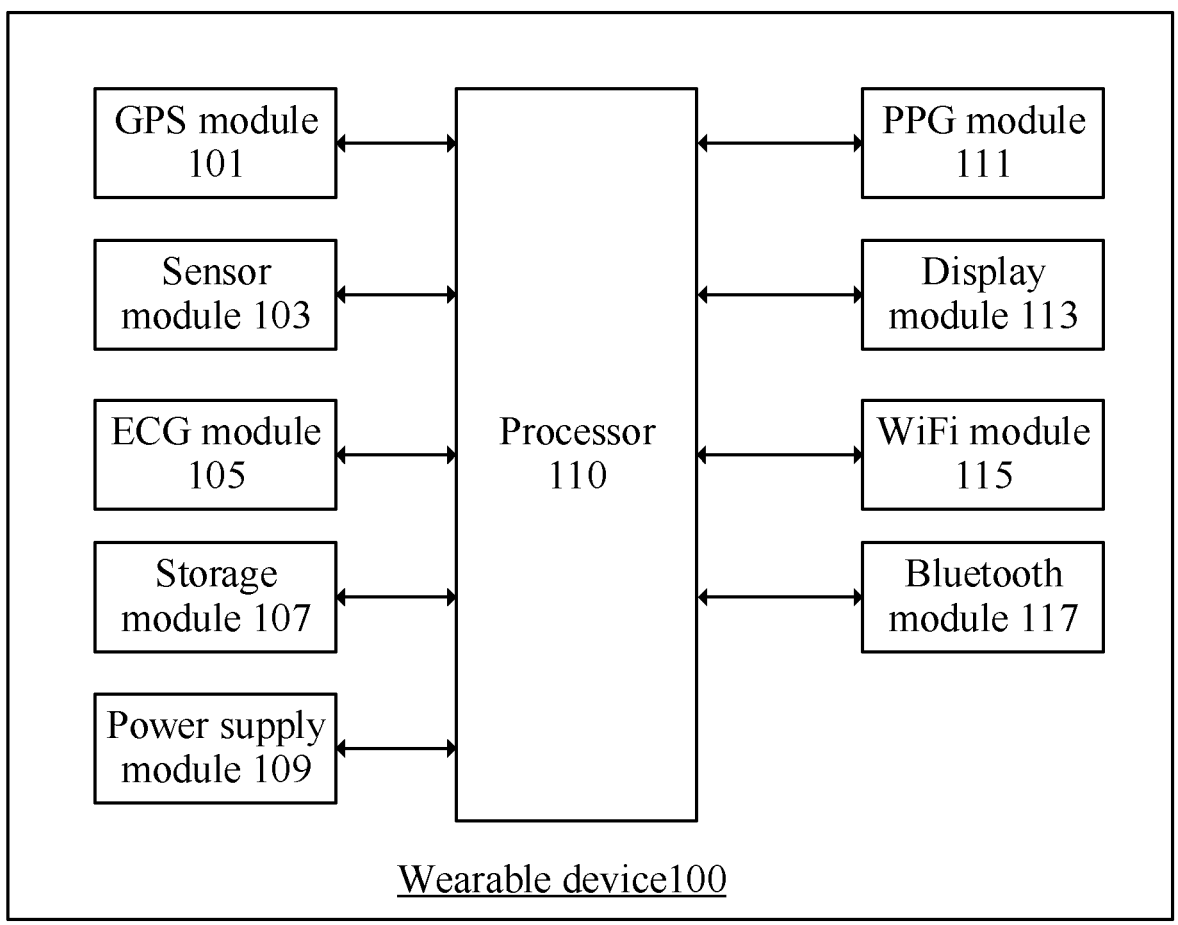
FIG. 1 is a block diagram of a wearable device according to an embodiment of the present application.

The technical schemes in embodiments of the present application will be described in conjunction with drawings in the embodiments of the present application.

Similar reference numerals and letters indicate similar items in the subsequent drawings, and therefore, once a certain item is defined in one drawing, the item needs no more definition and explanation in subsequent drawings. Meanwhile, in the description of the present disclosure, the terms including "first", "second", and the like are only configured to distinguish the description, and are not to be construed as indicating or implying relative importance.

An embodiment of the present application provides a method for controlling a wearable device. According to the method, an altitude change is measured in real time during the motion, a competition course is divided into multiple laps according to the altitude change and motion data is displayed in real time so as to assist a user to know the motion course, plan time, distribute physical strength, adjust motion intensity in time and complete the competition.

FIG. 1 is a block diagram of a wearable device according to an embodiment of the present application. As shown in FIG. 1, a wearable device 100 includes a processor 110, a global positioning system (GPS) module 101, a sensor module 103, an electrocardiography (ECG) module 105, a storage module 107, a power supply module 109, a photoplethysmography (PPG) module 111, a display module 113, a Wi-Fi module 115 and a Bluetooth module 117.

The GPS module 101 is configured to acquire position data of the wearable device 100. The position data includes, but is not limited to, longitude, latitude, altitude and time stamp. In some embodiments, the GPS module may send the position data to the processor 110. The processor 110 calculates a velocity of the user, such as a real-time horizontal velocity, according to the position data. In other embodiments, the real-time horizontal velocity calculated according to the position data may be used for calculating a climbing slope.

The sensor module 103 includes at least one of an accelerometer, a gyroscope, a magnetometer, a pulse oximeter, a barometer, a compass or an optical sensor.

The accelerometer is configured to measure accelerations of the wearable device on three axes (X-axis, Y-axis and Z-axis). In some embodiments, the acceleration may be used for measuring the velocity of the user in a vertical or horizontal direction. For example, in running, the acceleration may be used for measuring a real-time velocity (the real-time horizontal velocity) of the user in the horizontal direction during the motion. For another example, in mountaineering skiing, the acceleration may be used for measuring a real-time velocity (the real-time vertical velocity) of the user in the vertical direction during the motion.

The gyroscope is configured to measure a direction and angular velocity of the wearable device.

The magnetometer is configured to measure a magnetic field and a magnetic moment.

The pulse oximeter is configured to measure an oxygen saturation of the user.

The barometer is configured to acquire altitude data and air pressure data of the wearable device. In some embodiments, the barometer may be configured to calculate motion data of the user. The motion data includes the real-time vertical velocity, a single-lap vertical velocity, a single-lap climbing altitude, an accumulated climbing altitude and the like. For example, in sports such as mountaineering, mountaineering skiing or the like, the whole competition course is divided into multiple laps in the vertical or horizontal direction. During the motion, the user may know the motion course and the motion performance by data of each lap to plan the time, distribute the physical strength and adjust the motion intensity. It is to be noted that the mountaineering skiing described in the present application is just an example and not intended to limit the scope of the present application. All other embodiments obtained by those of ordinary skill in the art without creative work are within the scope of the present application.

In some embodiments, the barometer may include one or more resistances. The one or more resistances are configured to reduce the influence of temperature on the accuracy of the mbarometer. For example, when a temperature change causes an output voltage of the barometer to increase, the resistance value of the one or more resistances increases accordingly, causing that an output current of a constant current source is reduced, so that the output voltage of the barometer is reduced and restored to the original value. When the temperature change causes the output voltage of the barometer to decrease, the resistance value of the one or more resistances decreases accordingly, causing that the output current of the constant current source is increased, so that the output voltage of the barometer is increased and restored to the original value.

The compass is configured to measure a direction of the wearable device.

The optical sensor may be configured to detect an intensity of ambient light around the wearable device.

The ECG module 105 may be configured to acquire electrocardiographic data of the user. In some embodiments, the ECG module 105 may send the electrocardiographic data to the processor 110. The processor 110 may process the electrocardiographic data to generate heart rate data and heart rate variability data. In other embodiments, the ECG module 105 may also directly send the heart rate data and the heart rate variability data to the processor 110.

The storage module 107 may be configured to store data of the wearable device 100. The storage module 107 may include a flash memory and a random access memory. In some embodiments, the storage module 107 includes a non-transitory computer-readable storage medium storing computer instruction, where the computer instruction, when executed by a processor (such as the processor 110), causes the process to execute the method for controlling the wearable device disclosed in the present application.

The power supply module 109 is configured to supply power to the wearable device 100. In some embodiments, the power supply module 109 includes a photovoltaic module.

The PPG module 111 is configured to measure the heart rate and the oxygen saturation of the user.

The display module 113 is configured to display the motion data. In some embodiments, the wearable device 100 may be used for the mountaineering skiing. The competition course of the mountaineering skiing is divided into multiple laps in the vertical direction. If an altitude required to climb in the vertical direction of the whole competition course is 1500 meters, the user may configure a single-lap altitude (such as 500 meters per lap) to divide the competition course into multiple laps. During the motion, the user may know the competition process and the motion performance by the motion data displayed in the display module 113 to assist the user to plan the time and the physical strength. In some embodiments, the display module 113 may display the motion data such as the single-lap duration, the single-lap climbing altitude, the number of laps, the accumulated climbing altitude, the real-time vertical velocity, the single-lap vertical velocity and the slope.

The Wi-Fi module 115 is configured to communicate the wearable device 100 with an external device. In some embodiments, the wearable device 100 may update firmware by the Wi-Fi module 115. For example, the wearable device 100 may be connected to a smartphone by the Wi-Fi module 115. The smartphone may be configured to download a firmware file, and the smartphone may transmit the firmware to the wearable device 100 by the Wi-Fi module 115. The wearable device 100 may start upgrading the firmware after receiving the firmware file.

The Bluetooth module 117 is configured to communicate the wearable device 100 with the external device. In some embodiments, the Bluetooth module 117 may be configured to pair and communicate with the smartphone. For example, the Bluetooth module 117 may transmit the motion data of the user during the motion to the smartphone. The smartphone may be mounted with an application (APP) for analyzing the motion data. The APP may analyze the motion data in real time or periodically and generate corresponding visual icons to assist the user to analyze the motion performance after the user completes the motion.

Figure 2:
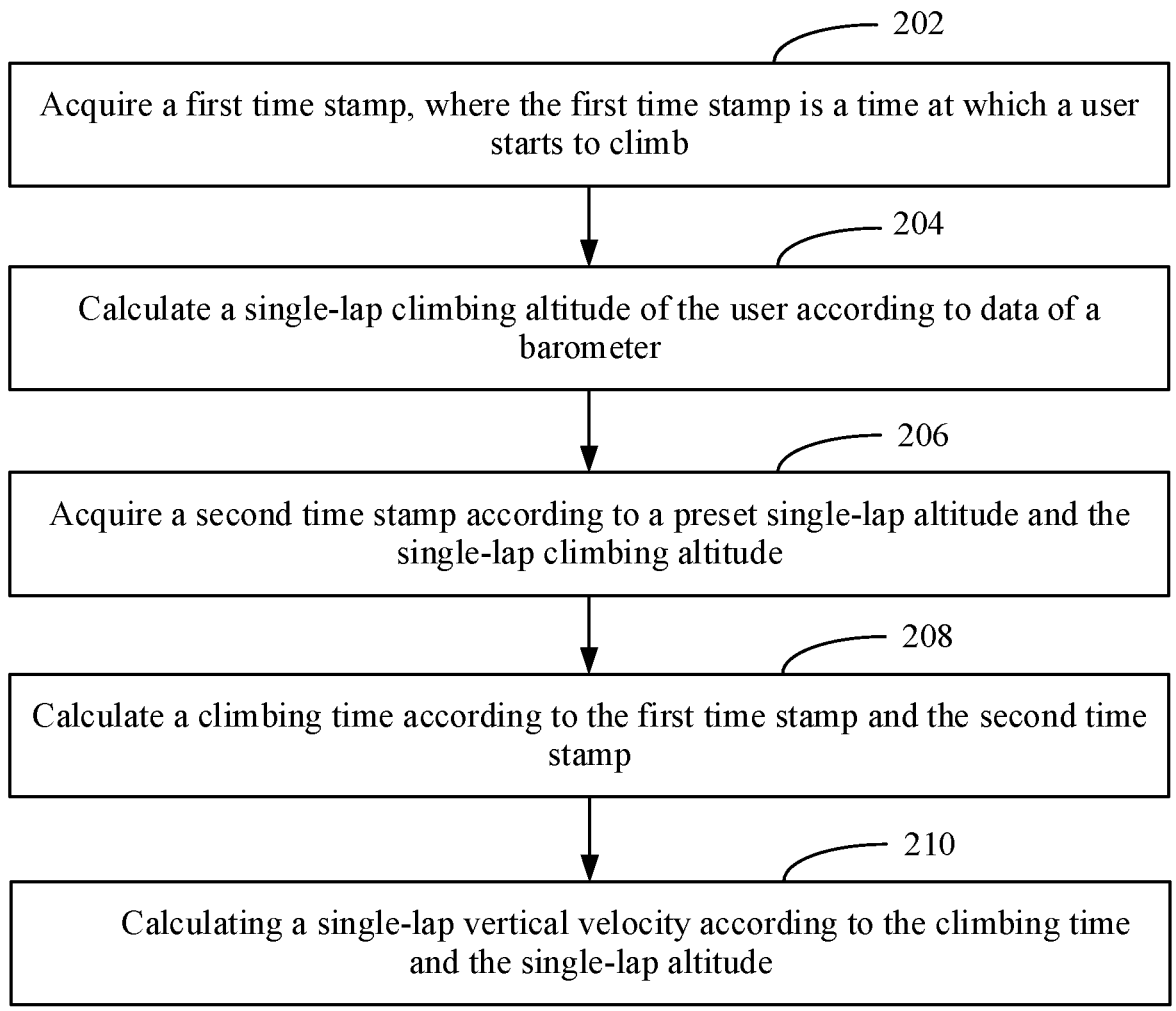
FIG. 2 is a flowchart of a method for controlling a wearable device according to an embodiment of the present application.

FIG. 2 is a flowchart of a method for controlling a wearable device according to an embodiment of the present application.

In some embodiments, the wearable device disclosed in the present application may execute the method for controlling the wearable device. Exemplarily, the processor 110 may acquire a first time stamp, where the first time stamp is a time at which a user starts climbing. The processor 110 may calculate a single-lap climbing altitude of the user according to data of a barometer. The processor 110 may acquire a second time stamp according to a preset single-lap altitude and the single-lap climbing altitude. The processor 110 may calculate a climbing time according to the first time stamp and the second time stamp. The processor 110 may calculate a single-lap vertical velocity according to the climbing time and the single-lap altitude.

In step 202, the first time stamp is acquired, where the first time stamp is the time at which the user starts climbing.

Figure 3:
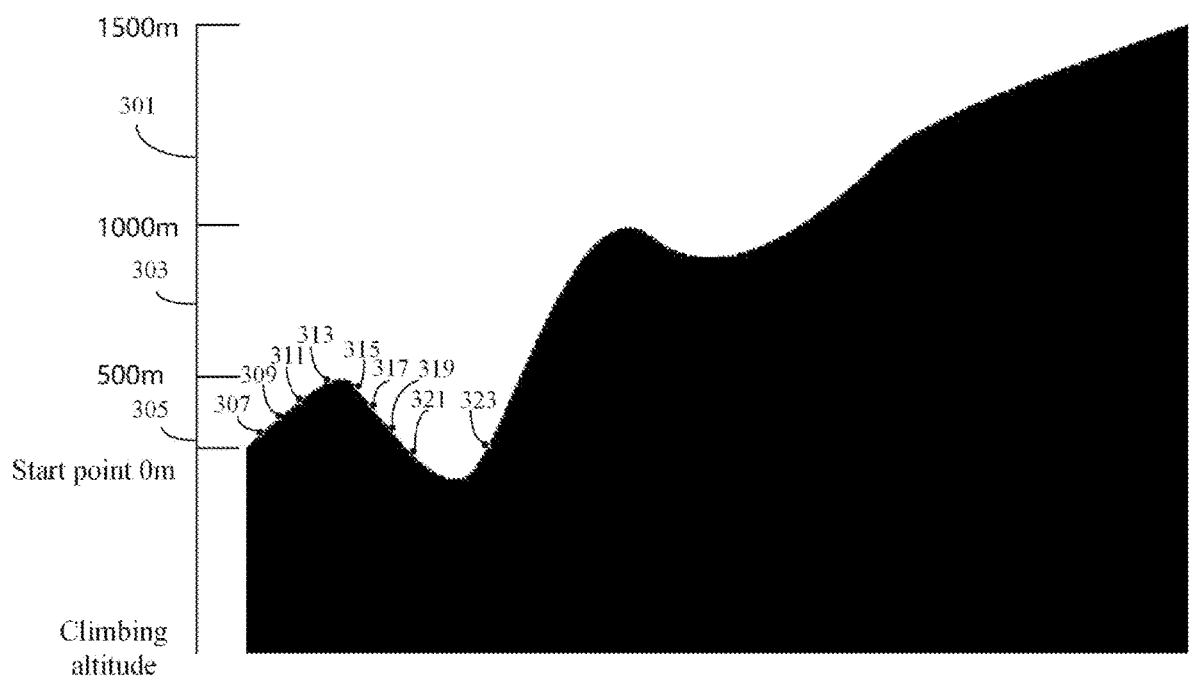
FIG. 3 is a schematic diagram of calculating a single-lap vertical velocity according to an embodiment of the present application.

In some embodiments, the processor 110 may acquire the first time stamp, where the first time stamp is the time at which the user starts climbing. Referring to FIG. 3, FIG. 3 is a schematic diagram of calculating a single-lap vertical velocity according to an embodiment of the present application. The motion data includes the single-lap climbing altitude, the accumulated climbing altitude, the single-lap vertical velocity, the real-time vertical velocity. FIG. 3 shows that a competition course (the accumulated climbing altitude) of a sport (such as climbing, or mountaineering skiing) in the vertical direction is divided into multiple laps. The competition course in the vertical direction in FIG. 3 is totally 1500 m, and is divided into a single lap 301, a single lap 303 and a single lap 305 according to a single-lap altitude of 500 m. In some embodiments, the user may start climbing at 0 m, the first time stamp is determined to be the time at which the user starts climbing by the wearable device 100.

In some embodiments, the climbing may be divided into a climbing recognition stage and a climbing stage. At the climbing recognition stage, the wearable device 100 may determine that the user starts climbing by recording the first time stamp. At the climbing stage, the wearable device 100 may calculate the accumulated climbing altitude and the single-lap climbing altitude by accumulating altitude changes after the first time stamp. For example, the wearable device 100 may calculate the accumulated climbing altitude and the single-lap climbing altitude according to the data of the barometer.

In some embodiments, the wearable device 100 may determine the first time stamp by the data of the barometer. The barometer of the wearable device 100 may acquire multiple sampling points during the motion of the user. Referring to FIG. 3, nine sampling points, sampling points 307, 309, 311, 313, 315, 317, 319, 321 and 323, are sampling points acquired by the barometer during the motion of the user. Each sampling point includes the altitude data. The wearable device 100 may determine the first time stamp by an accumulated altitude change of the multiple sampling points. For example, the wearable device 100 may determine the first time stamp by calculating altitude changes of adjacent sampling points among the sampling points 307 to 313. An ascending altitude is counted as positive and a descending altitude is counted as negative. In an embodiment, an altitude change from the sampling point 307 to the sampling point 309 is +2, an altitude change from the sampling point 309 to the sampling point 311 is +3, and an altitude change from the sampling point 311 to the sampling point 313 is +3.5, so that the accumulated altitude change is 8.5. After the accumulated altitude change is calculated, the wearable device may compare the accumulated altitude change with a first threshold, and if the accumulated altitude change is greater than the first threshold (for example, the first threshold is 1), it is determined that the user starts climbing, and a corresponding time stamp is marked as the first time stamp. Exemplarily, the wearable device may calculate the accumulated climbing altitude by the accumulated altitude change. For example, an initial value of the accumulated climbing altitude is 0. After the wearable device determines that the user starts climbing, the accumulated climbing altitude may be added to the accumulated altitude change (0+8.5) to calculate the accumulated climbing altitude in real time. In other embodiments, the wearable device may calculate the single-lap climbing altitude by the accumulated altitude change. For example, an initial value of the single-lap climbing altitude is 0. After the wearable device determines that the user starts climbing, the single-lap climbing altitude may be added to the accumulated altitude change (0+8.5) to calculate the single-lap climbing altitude in real time.

In some embodiments, the wearable device may calculate an accumulated climbing by the accumulated altitude change. For example, the initial value of the accumulated climb altitude is 0 and after entering the climbing stage, the wearable device may add the accumulated climbing to the altitude change to calculate the accumulated climbing altitude in real time. In other embodiments, when the altitude change is lower than a third threshold (such as −1 m), the wearable device may clear the altitude change to prevent the accumulated climbing altitude from being overridden in case the user descends.

In some embodiments, the wearable device may monitor the accumulated altitude change in real time. For example, the wearable device may return to the climbing recognition stage when the accumulated altitude change descends to a fourth threshold (such as 0.5 m), which can improve the sensitivity of the climb monitoring.

It is to be noted that the above description of the first threshold is just an example and is not intended to limit the scope of the present application. All other embodiments obtained by those of ordinary skill in the art without creative work are within the scope of the present application. Setting of the first threshold and the third threshold is related to a noise level of the barometer, and different barometers may flexibly set the first threshold and the third threshold according to the noise level.

In step 204, the single-lap climbing altitude of the user is calculated according to the data of the barometer.

In some embodiments, the processor 110 may calculate the single-lap climbing altitude of the user according to the data of the barometer. The single-lap climbing altitude refers to a real-time accumulated climbing altitude of the user within a single lap, such as a real-time accumulated climbing altitude of the user within the single lap 305.

In some embodiments, after the first time stamp is acquired, the processor 110 may receive the data from the barometer to calculate the single-lap climbing altitude of the user. In an embodiment, the processor 110 may calculate the single-lap climbing altitude by accumulating the accumulated altitude change. For example, the initial value of the single-lap climbing altitude is 0. Referring to FIG. 3, the processor 110 determines that the user starts climbing at the sampling point 307 (the first time stamp), and the processor 110 may accumulate altitude changes of the sampling points 307 to 313 to calculate the single-lap climbing altitude. For example, the altitude change from the sampling point 307 to the sampling point 309 is +3, the altitude change from the sampling point 309 to the sampling point 311 is +7, and the altitude change from the sampling point 311 to the sampling point 313 is +5, so that the processor 110 may calculate that a single-lap climbing altitude of the user at the sampling point 313 is 15 m. For example, the height change from the sample point 307 to the sample point 309 is +3, the height change from the sample point 309 to the sample point 311 is +7, and the height change from the sample point 311 to the sample point 313 is +5, so that the processor 110 may calculate that a single lap climb height of the user at the sample point 313 is 15 m.

In some embodiments, the barometer collects the data at a fixed or variable frequency. For example, the barometer may collect the data at a frequency of 1 Hz. It is to be noted that the above description of the collection frequency of the barometer is just an example and is not intended to limit the scope of the present application. All other embodiments obtained by those of ordinary skill in the art without creative work are within the scope of the present application.

In some embodiments, the barometer may calculate the altitude using current air pressure data and sea-level pressure data, or may calculate sea-level pressure data using the current air pressure data and the altitude. In other embodiments, the barometer may automatically switch between an altimeter mode and a barometer mode based on a speed of the altitude change during the motion. For example, in the altimeter mode, the altitude of the barometer varies continuously but a sea-level pressure remains unchanged. In the barometer mode, the sea-level pressure of the barometer varies continuously but the altitude remains unchanged. The above embodiment can avoid the phenomenon of altitude drifting due to the sea-level pressure change during the motion.

In some embodiments, the wearable device 100 may include a filter for filtering the data of the barometer. For example, the filter may be a low-pass filter which may set a cutoff frequency. The lower the cutoff frequency is, the smoother the data of the barometer will be, but the change trend can also lag behind. In some embodiments, the wearable device 100 may automatically adjust the cutoff frequency according to a horizontal velocity and/or a vertical velocity, such as the real-time vertical velocity or the single-lap vertical velocity, to ensure stability and instantaneity of the data of the barometer. For example, the wearable device 100 may turn down the cutoff frequency when the vertical velocity is relatively low and may turn up the cutoff frequency when the vertical velocity is high.

In step 206, the second time stamp is acquired according to the preset single-lap altitude and the single-lap climbing altitude.

In some embodiments, the processor 110 may acquire the second time stamp according to the preset single-lap altitude and the single-lap climbing altitude. The second time stamp is used for indicating a time at which the user's climbing within a single lap ends. Referring to FIG. 3, the single-lap altitude is set to be 500 m, and the processor 110 may monitor the single-lap climbing altitude in real time to determine whether a difference between the single-lap climbing altitude and the single-lap altitude is less than a second threshold. For example, when the second threshold is 5 and the difference between the single-lap climbing altitude and the single-lap altitude is less than 5, the second time stamp is recorded. For another example, when the second threshold is 0 and the difference between the single-lap climbing altitude and the single-lap altitude is less than 0, the second time stamp is recorded.

In some embodiments, the processor 110 may clear the single-lap climbing altitude after the second time stamp is acquired. Referring to FIG. 3, the initial value of the single-lap climbing altitude is 0 at the beginning of the single lap 305. At the end of the single lap 305, that is, when the processor 110 acquires the second time stamp, the single-lap climbing altitude is 500. In this case, after the second time stamp is acquired, the processor 110 may clear the single-lap climbing altitude to start calculating the single-lap climbing altitude of a next lap (the single lap 303).

In some embodiments, after the second time stamp is determined, the wearable device 100 may remind the user that the lap ends. For example, the wearable device 100 may remind the user that the lap ends by vibration, buzzer or the like.

In step 208, the climbing time is calculated according to the first time stamp and the second time stamp.

In some embodiments, the processor 110 may calculate the climbing time according to the first time stamp and the second time stamp. For example, the processor 110 may subtract the first time stamp from the second time stamp to calculate the climbing time.

In step 210, the single-lap vertical velocity is calculated according to the climbing time and the single-lap altitude.

In some embodiments, the processor 110 may calculate the single-lap vertical velocity according to the climbing time and the single-lap altitude. For example, the processor 110 may divide the single-lap altitude by the climbing time to calculate the single-lap vertical velocity.

In some embodiments, the processor 110 may calculate the real-time vertical velocity of the user. Exemplarily, the processor 110 may calculate the real-time vertical velocity by a preset time window. For example, the time window is set to be ten seconds, and the processor 110 may calculate the real-time vertical velocity according to a current altitude, an altitude before ten seconds and the time window.

In some embodiments, the processor 110 may calculate a slope. Exemplarily, the processor 110 may acquire the real-time horizontal velocity of the user by a GPS module, such as the GPS module 101. The processor 110 may calculate the slope by the real-time horizontal velocity and the real-time vertical velocity, such as the real-time vertical velocity/real-time horizontal velocity * 100. In other embodiments, if the real-time horizontal velocity is 0, slope information is not showed.

In the method for controlling the wearable device disclosed in the present application, the motion data such as the single-lap climbing altitude, the accumulated climbing altitude and the single-lap vertical velocity is calculated by using the barometer to more accurately reflect the motion process dominated by a vertical displacement, thereby assisting the user to plan the time and distribute the physical strength, adjust motion intensity and complete the competition.

FIGS. 4 to 8 are schematic diagrams of a display interface according to an embodiment of the present application. In some embodiments, the wearable device disclosed in the present application (such as the wearable device 100) may be configured to display the data in FIGS. 4 to 8. Exemplarily, after acquiring the motion data, the processor 110 may send the motion data to the display module 113 to display the motion data.

Figure 4:
FIG. 4 is a schematic diagram of a user interface of a wearable device according to an embodiment of the present application.

Referring to FIG. 4, the wearable device disclosed by the present application may output current data on a display module (such as the display module 113) when the user completes the single lap. In some embodiments, the wearable device may display a single-lap duration, a single-lap ascending (i.e., the single-lap altitude) and the number of laps (such as a first lap).

Figure 5:
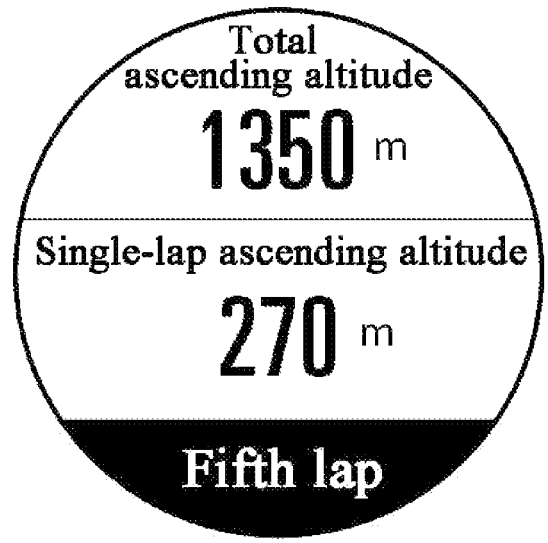
FIG. 5 is a schematic diagram of a user interface of a wearable device according to an embodiment of the present application.

Referring to FIG. 5, the wearable device disclosed by the present application may display data (such as the accumulated climbing altitude and the single-lap climbing altitude) related to the altitude during the motion. In some embodiments, the wearable device may display the accumulated climbing altitude, the single-lap climbing altitude and the number of laps (such as a fifth lap).

Figure 6:
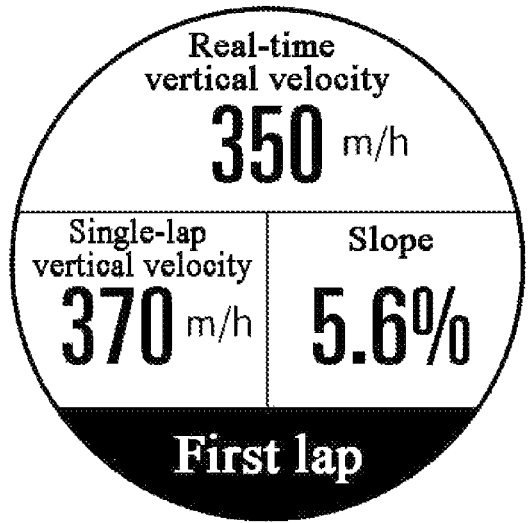
FIG. 6 is a schematic diagram of a user interface of a wearable device according to an embodiment of the present application.

Referring to FIG. 6, the wearable device disclosed by the present application may display the motion data in real time during the motion. In some embodiments, the wearable device may display the real-time vertical velocity, the single-lap vertical velocity, the slope and the number of laps (such as the first lap). The user may know a current motion state in time by the motion data to flexibly adjust the motion intensity. For example, if the user finds that the real-time vertical velocity is less than the single-lap vertical velocity, the user can speed up appropriately. If the user finds that the real-time vertical velocity is greater than the single-lap vertical velocity, the user can slow down appropriately.

Figure 7:
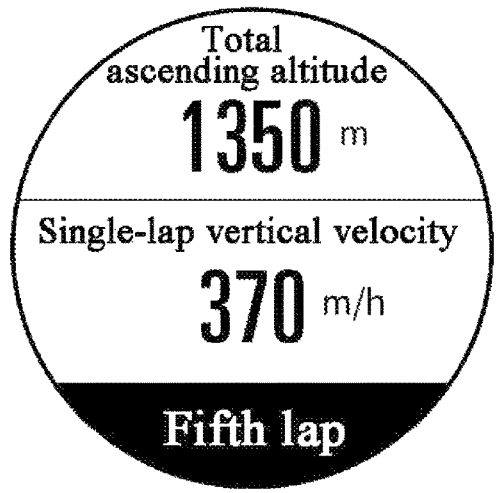
FIG. 7 is a schematic diagram of a user interface of a wearable device according to an embodiment of the present application.

Referring to FIG. 7, the wearable device disclosed in the present application may display the motion data in real time during the motion. In some embodiments, the wearable device may display the accumulated climbing altitude, the single-lap vertical velocity, and the number of laps (such as the fifth lap). The user may know the execution of the user's motion strategy by the motion data. If the user's motion strategy in a long-distance running is to be slow first and then fast, the user may adjust the motion state by the motion data and climb at a relatively low single-lap vertical velocity (such as 370 m/h) at an initial stage of the competition course to reserve the physical strength to sprint at a higher velocity (such as 500 m/h) at a latter stage of the competition course.

Figure 8:
FIG. 8 is a schematic diagram of a user interface of a wearable device according to an embodiment of the present application.

Referring to FIG. 8, FIG. 8 is a schematic diagram of a switching interface between two laps according to an embodiment of the present application. The wearable device disclosed by the present application may display the single-lap duration, the single-lap climbing altitude, the accumulated climbing altitude and the number of laps at the end of one lap. The wearable device may clear the single-lap climbing altitude at the beginning of the next lap to start calculating a single-lap climbing altitude of the next lap. It is to be noted that the single-lap climbing altitude represents the accumulated climbing altitude of the user within one lap, and the accumulated climbing altitude represents an accumulated climbing altitude of the user climbing from the beginning to a current position. The single-lap climbing altitude is cleared when the user finishes climbing within one lap and enters the next lap.

The devices and methods disclosed in the embodiments of the present application may be implemented in other manners. The preceding device embodiments are merely illustrative.

For example, the flowcharts and block diagrams in the drawings illustrate possible implementation of architectures, functions and operations of the devices, methods and computer program products according to the embodiments of the present application. In this regard, each block in a flowchart or block diagram may represent a module, a program segment, or part of codes that contains one or more executable instructions for implementing specified logical functions. In some alternative implementations, the functions marked in the blocks may occur in an order different than those marked in the drawings. For example, two sequential blocks may, in fact, be executed substantially concurrently, or sometimes executed in the reverse order, which depends on the involved functions. It is to be noted that each block in the block diagrams and/or flowcharts, and combinations of blocks in the block diagrams and/or flowcharts may be implemented by not only specific-purpose hardware-based systems that perform specified functions or actions, but also combinations of specific-purpose hardware and computer instructions.

Additionally, functional modules in the embodiments of the present application may be integrated together to form an independent part, or each module may exist alone, or two or more modules may be integrated to form an independent part.

The functional modules may be stored in a non-transitory computer-readable storage medium if implemented in the form of software function modules and sold or used as independent products. Based on this understanding, the technical schemes in the present application substantially, the part contributing to the existing art, or part of the technical schemes, may be embodied in the form of a software product. This computer software product is stored on a storage medium, and includes several instructions for enabling a computer device (which may be a personal computer, a server, a network device or the like) to perform all or part of the steps in the methods in embodiments of the present application. The preceding storage medium includes a universal serial bus (USB) flash disk, a mobile hard disk, a read-only memory (ROM), a random access memory (RAM), a magnetic disk, an optical disk or another medium capable of storing program codes.

What is claimed is:

1. A method for controlling a wearable device, comprising:
   acquiring a first time stamp, wherein the first time stamp is a time at which a user starts climbing;
   calculating a single-lap climbing altitude of the user according to data of a barometer; wherein calculating the single-lap climbing altitude of the user according to the data of the barometer comprising: using a filter included in the wearable device to filter the data of the barometer, and calculating the single-lap climbing altitude of the user according to the filtered data of the barometer;
   acquiring a second time stamp according to a preset single-lap altitude and the single-lap climbing altitude;
   calculating a climbing time according to the first time stamp and the second time stamp;
   calculating a single-lap vertical velocity according to the climbing time and the single-lap climbing altitude;
   calculating a real-time vertical velocity of the user according to a preset time window; and
   adjusting a cutoff frequency of the filter according to the single-lap vertical velocity or the real-time vertical velocity.

2. The method of claim 1, wherein acquiring the first time stamp comprises:
   acquiring a plurality of sampling points from the barometer;
   calculating an accumulated altitude change of the plurality of sampling points; and
   determining the first time stamp according to the accumulated altitude change and a first threshold.

3. The method of claim 1, wherein acquiring the second time stamp comprises:
   determining the second time stamp in response to determining that a difference between the preset single-lap altitude and the single-lap climbing altitude is less than or equal to a second threshold.

4. The method of claim 1, further comprising:
   filtering the data of the barometer according to the real-time vertical velocity.

5. A wearable device, comprising:
   a barometer; and
   a processor, which is configured to:
   acquire a first time stamp, wherein the first time stamp is a time at which a user starts climbing;
   calculate a single-lap climbing altitude of the user according to data of a barometer;
   acquire a second time stamp according to a preset single-lap altitude and the single-lap climbing altitude;
   calculate a climbing time according to the first time stamp and the second time stamp;
   calculate a single-lap vertical velocity according to the climbing time and the single-lap climbing altitude,
   wherein the processor is further configured to:
   use a filter included in the wearable device to filter the data of the barometer, and calculate the single-lap climbing altitude of the user according to the filtered data of the barometer;
   calculate a real-time vertical velocity of the user according to a preset time window; and
   adjust a cutoff frequency of the filter according to the single-lap vertical velocity or the real-time vertical velocity.

6. The wearable device of claim 5, wherein the processor is further configured to:
   acquire a plurality of sampling points from the barometer;
   calculate an accumulated altitude change of the plurality of sampling points; and
   determine the first time stamp according to the accumulated altitude change and a first threshold.

7. The wearable device of claim 5, wherein the processor is further configured to:
   determine the second time stamp in response to determining that a difference between the preset single-lap altitude and the single-lap climbing altitude is less than or equal to a second threshold.

8. The wearable device of claim 5, wherein the processor is further configured to:
   filter the data of the barometer according to the real-time vertical velocity.

9. A non-transitory computer-readable storage medium storing a computer instruction, wherein the computer instruction, when executed by a processor, implements a method for controlling a wearable device, and the method comprises:
   acquiring a first time stamp, wherein the first time stamp is a time at which a user starts climbing;
   calculating a single-lap climbing altitude of the user according to data of a barometer;
   acquiring a second time stamp according to a preset single-lap altitude and the single-lap climbing altitude; wherein calculating the single-lap climbing altitude of the user according to the data of the barometer comprising: using a filter included in the wearable device to filter the data of the barometer, and calculating the single-lap climbing altitude of the user according to the filtered data of the barometer;
   calculating a climbing time according to the first time stamp and the second time stamp;
   calculating a single-lap vertical velocity according to the climbing time and the single-lap altitude;
   calculating a real-time vertical velocity of the user according to a preset time window; and
   adjusting a cutoff frequency of the filter according to the single-lap vertical velocity or the real-time vertical velocity.

10. The non-transitory computer-readable storage medium of claim 9, wherein acquiring the first time stamp comprises:
    acquiring a plurality of sampling points from the barometer;
    calculating an accumulated altitude change of the plurality of sampling points; and
    determining the first time stamp according to the accumulated altitude change and a first threshold.

11. The non-transitory computer-readable storage medium of claim 9, wherein acquiring the second time stamp comprises:
    determining the second time stamp in response to determining that a difference between the preset single-lap altitude and the single-lap climbing altitude is less than or equal to a second threshold.

12. The non-transitory computer-readable storage medium of claim 9, wherein the method further comprises:
    filtering the data of the barometer according to the real-time vertical velocity.

* * * * *